United States Patent [19]

Dolak et al.

[11] Patent Number: 4,505,911
[45] Date of Patent: Mar. 19, 1985

[54] ISOINDOLE DIURETIC DERIVATIVES, COMPOSITIONS AND USE

[75] Inventors: Terence M. Dolak; Tellis A. Martin, both of Evansville, Ind.

[73] Assignee: Mead Johnson & Company, Evansville, Ind.

[21] Appl. No.: 541,400

[22] Filed: Oct. 13, 1983

[51] Int. Cl.³ .............. A61K 31/40; A61K 31/535; C07D 209/46; C07D 413/06
[52] U.S. Cl. .................... 514/229; 514/323; 514/339; 544/144; 546/200; 546/272; 548/472
[58] Field of Search ........... 544/144; 546/200, 272; 548/472; 424/248.5, 263, 267, 274

[56] References Cited

U.S. PATENT DOCUMENTS 3,183,243  5/1965  Lee et al. .................. 548/472
3,579,524  5/1971  Van Dyke, Jr. ............ 424/267

FOREIGN PATENT DOCUMENTS 26749  8/1981  European Pat. Off. .

OTHER PUBLICATIONS

Cornish, et al., J. Pharm. Pharmacol., 18, (1966), pp. 65–80.
Himori, et al., Jpn. J. Pharmacol, 1978, 28(6), pp. 811–818, (Chem. Abs. 90:97589t).
Suzuki, et al., Nippon Yakurigaku Zasshi, 1972, 68(3), pp. 276–289, (Chem. Abs. 81: 58265d).

Primary Examiner—Robert W. Ramsuer
Attorney, Agent, or Firm—Robert H. Uloth; Richard P. Ryan

[57] ABSTRACT

The invention provides 3-oxoisoindole compounds useful as diuretics of the general formula

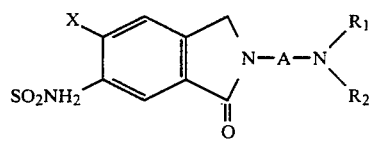

wherein X is halogen or trifluoromethyl, A is alkylene ($C_2$–$C_4$), $R_1$ is alkyl, $R_2$ is alkyl or phenylalkyl, or $R_1$ and $R_2$ taken together with nitrogen are piperidino, morpholino or pyridinyl.

14 Claims, No Drawings

ISOINDOLE DIURETIC DERIVATIVES, COMPOSITIONS AND USE

FIELD OF THE INVENTION

This invention relates to isoindole derivatives, pharmaceutically acceptable salts thereof and to processes for synthesis thereof. Other aspects of the invention concern pharmaceutical compositions containing an instant compound as active ingredient and method of treatment where there is an indicated need for a diuretic agent.

DESCRIPTION OF THE PRIOR ART

European Patent Application No. 26,749 discloses 2-(benzylpiperidinyl)-phthalimidine derivatives useful as antipsychotic agents of the following general formula (1)

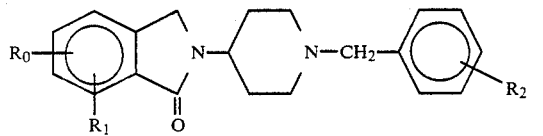

wherein $R_0$, $R_1$, and $R_2$ are independently hydrogen, halogen, $C_{1-3}$ alkyl, $C_{1-3}$ alkoxy, or trifluoromethyl. The compounds of (1) are reportedly neuropharmacologically active and useful for treating psychotic disorders, especially schizophrenia and mania.

Cornish, et al, J. Pharm. Pharmacol., 18, 65–80 (1966) disclose preparation of phthalimides and 1-oxoisoindolines related to the diuretic clorexolone (2).

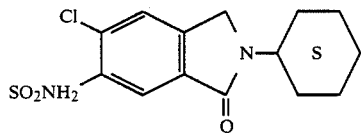

Himori, et al, Jpn. J. Pharmacol. 1978, 28(6), 811–818; (Chem. Abs. 90:97589t) studied the antihypertensive effect of a combination of clorexolone and the β-adrenergic blocking agent, alprenolol in conscious renal hypertensive dogs and found a significant decrease in blood pressure after the second day of treatment.

Suzuki, et al, Nippon Yakurigaku Zasshi, 1972, 68(3), 276–289 (Chem. Abs. 81:58265d) reported that the hypotensive diuretics, hydroflumethiazide, triamterene, clorexolone, etc. have favorable effects in the spontaneously hypertensive rat.

U.S. Pat. No. 3,579,524 to Van Dyke, Jr. discloses aminoalkyl derivatives of phthalimidine of general formula (3)

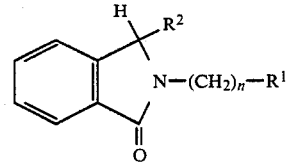

wherein n is 2 to 5, $R^2$ is H and OH, and $R^1$ amino nitrogen is part of a heterocyclic moiety such as piperidinyl, morpholinyl, piperazinyl, etc. The compounds are said to be antihypertensive agents producing a gradual decrease in blood pressure in dogs.

SUMMARY AND DETAILED DESCRIPTION OF THE INVENTION

In its broadest aspect, the present invention is concerned with 3-oxoisoindole derivatives having diuretic properties characterized by a compound of Formula I

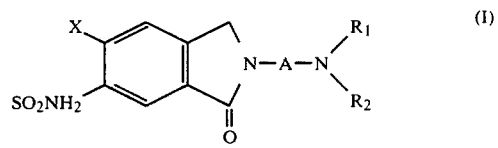

wherein X is halogen or trifluoromethyl; A is an alkylene radical of 2 to 4 carbon atoms inclusive; $R_1$ is lower alkyl; $R_2$ is lower alkyl or phenylalkyl of 7 to 10 carbon atoms; or $R_1$ and $R_2$ taken together with the nitrogen to which they are attached may be piperidino, morpholino or pyridinyl; or a pharmaceutically acceptable acid addition salt thereof.

It is to be understood that by the term "lower alkyl" and "lower alkoxy" used herein, it is meant both straight and branched carbon radicals containing from 1 to 6 carbon atoms, preferably not more than 4 carbon atoms. Exemplary of carbon chain radicals are methyl, ethyl, isopropyl, 1-butyl, 1-methylpropyl, 2-methylpropyl, tert.-butyl, hexyl and the like. The term "alkylene" as used herein refers to a branched or preferably straight chain divalent radical of 2 to 4 carbon atoms. Further the term "halogen" used herein connotes all members of that group but preferably chlorine, bromine and fluorine. The term phenylalkyl comprehends such radicals as benzyl, phenethyl, phenylpropyl, phenylisopropyl and the like.

The pharmaceutically acceptable acid addition salts of the invention are those in which the anion does not contribute significantly to toxicity or pharmacological activity of the salt, and therefore are considered pharmacological equivalents of Formula I bases.

For purposes of salt formation of the substances of Formula I, there may be mentioned pharmaceutical acceptable acids such as hydrochloric and other hydrohalic acids, sulphuric, phosphoric, nitric, aliphatic, alicyclic, aromatic or heterocyclic carboxylic acids or sulphonic acids, such as formic, acetic, propionic, succinic, glycollic, lactic, malic, tartaric, citric, ascorbic, maleic, hydroxymaleic or pyruvic, fumaric, benzoic, p-amino-benzoic, anthranilic, p-hydroxybenzoic, salicyclic, or p-aminosalicyclic, methanesulphonic, ethanesulphonic, hydroxyethanesulphonic, ethylenesulphonic; halogenobenzenesulphonic acid, toluenesulphonic acid, naphthalenesulphonic acid or sulphanilic acid.

Conventional methods are used to prepare the salts. Thus, admixture of a Formula I base with the selected acid in an inert solvent such as water, ethyl acetate, methanol, dimethylformamide and the like with salt isolation by conventional concentration or crystallization techniques are employed. The Formula I salts are, in some instances, obtained in hydrated form, e.g., hemihydrates, monohydrates, sesquihydrates; and it is to be understood that such forms are within the ambit of the instant invention.

According to the present invention, the compounds characterized by Formula I

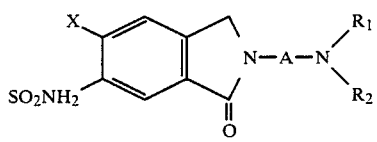

wherein X is halogen or trifluoromethyl; A is a divalent straight or branched chain alkylene radical of 2 to 4 carbon atoms inclusive, $R_1$ is lower alkyl; $R_2$ is lower alkyl or phenylalkyl of 7 to 10 carbon atoms; or $R_1$ and $R_2$ taken together with the nitrogen to which they are attached may be piperidino, morpholino or pyridinyl are obtained by a method comprising (a) reducing a 1,3-dioxoisoindole compound of Formula II or a 1-hydroxy-3-oxoisoindole compound of Formula III

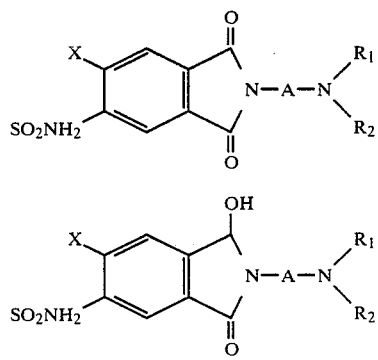

wherein X, A, $R_1$ and $R_2$ are as defined above; or (b) reacting a 4-aminopiperidine compound of Formula IV

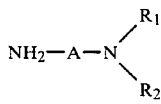

wherein A, $R_1$ and $R_2$ are as defined above with a sulfamoyl compound of Formula V in an inert solvent

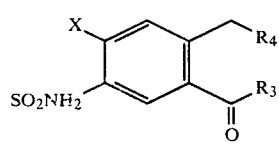

wherein X is as defined above, $R_3$ is amino, halogen, lower alkoxy; and $R_4$ is halogen or taken as the radical $R_4CH_2$— is carbamoyl or formyl; and $R_3$ and $R_4$ taken together is oxygen.

Reduction of the 1,3-dioxoisoindole compounds of Formula II or 1-hydroxy-3-oxoisoindoles of Formula III is carried out with zinc and acetic acid or tin and concentrated hydrochloric acid at elevated temperatures generally ranging from 60°–150° for periods of about 6–48 hours in a reaction inert organic solvent. In the case of zinc-acetic acid, temperatures of 100°–150° are preferred and the reduction is conveniently carried out in acetic acid at reflux temperature. The compounds of Formula I obtained by reduction with zinc-acetic acid are purified by conventional techniques such as basification, extraction and trituration of the extract or precipitation of acid addition salts from crude extracts. In the case of the tin/concentrated hydrochloric acid reduction, preferably carried out at 60°–100° in methanol, the Formula I products form relatively stable complexes with tin salts and purification is carried out by treating the tin complexed Formula I products with hydrogen sulfide under acidic conditions or tetramethylethylenediamine in an inert solvent such as methanol to precipitate the tin as the insoluble sulfide or tetramethylethylenediamine complex, respectively. Reduction of Formula II and Formula III compounds may be carried out by other conventional means such as use of light metal hydrides.

The compounds of Formula III considered part of the present invention are obtained by reduction of the corresponding 1,3-dioxoisoindole with excess zinc in acetic acid below 100°, preferably at or near room temperature.

The intermediates of Formula IV are generally known to the art or prepared by art-recognized methods.

It is to be understood that the sulfamoyl intermediates of Formula V particularly comprehend such compounds as:

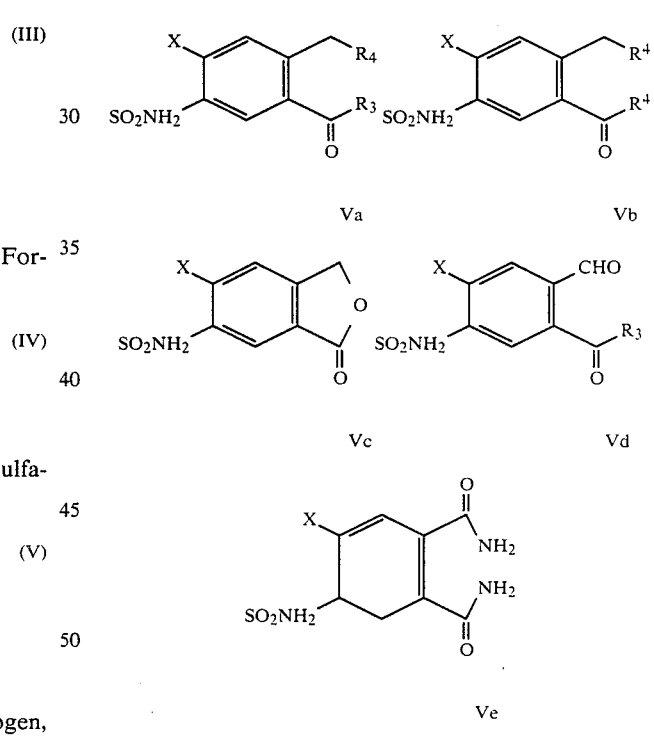

wherein X is halogen or trifluoromethyl, $R_3$ is lower alkoxy, preferably methoxy and $R_4$ is halogen.

Known methods are employed in preparation of Formula V intermediates as illustrated by European Patent Application No. 26,749, supra.

The compounds of Formula I have diuretic properties as can be demonstrated by standard pharmacological test models known to correlate with effects in man. By way of example, there can be mentioned the conscious rat diuretic screen of Lipschitz, et al (J. Pharmacol. Exp. Therap. 79, 97 (1943)). In this test, dose response assays of diuretic, naturiretic and kaliuretic activity are determined by oral administration of the test substance with the compounds of Formula I exhibiting significant diuretic properties at doses ranging from 0.3 to 30 mg/kg body weight.

As stated above, Formula I compounds have diuretic properties. Thus, another embodiment of the instant invention is directed to a process comprising systemically administering to a mammal in need of diuresis a diuretic effective amount of a compound of Formula I or a pharmaceutically acceptable acid addition salt thereof. By systemic administration, it is intended to include both oral and parenteral routes with oral being preferred. Examples of parenteral administration are intramuscular, intravenous, intraperitoneal, rectal and subcutaneous administration. The dosage will vary with the form of administration and the particular compound chosen. However, from about 0.05 to 50 mg. per kg. of body weight of a mammal of a compound characterized by Formula I administered in effective single or multiple dosage units is generally satisfactory. In accordance with conventional clinical practice, a diuretic agent of Formula I is administered at a dosage substantially less than the dose of the compound which is thought to be effective. If the diuretic response is insufficient after a suitable trial, dosage is increased by small increments until the optimum diuretic effect is reached. In most cases, optimum doses fall within a range of 0.05 to 25 mg. per kg. or 0.05 to 10 mg. per kg. of body weight and it is contemplated that the Formula I compounds can be used in the same manner as the clinically useful thiazides and related compounds described in *AMA Drug Evaluations*, 750–753 (American Medical Association, Chicago, Ill., Fifth Edition).

In carrying out the diuretic process, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention. All temperatures are degrees centigrade and melting points taken with a Thomas Hoover capillary apparatus are uncorrected. Conventional abbreviations are employed in reporting nuclear magnetic resonance (NMR) spectral data with tetramethylsilane as internal reference and chemical shift data values in parts per million.

EXAMPLE 1

6-Chloro-2,3-dihydro-3-oxo-2-(2-pyridinylmethyl)-1H-isoindole-5-sulfonamide

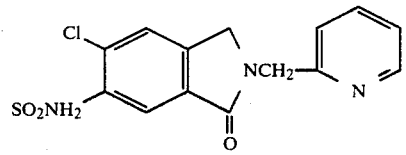

(a) 6-Chloro-2,3-dihydro-1,3-dioxo-2-(2-pyridinylmethyl)-1H-isoindole-5-sulfonamide. A mixture of 4-chloro-5-sulfamoylphthalimide (8.4 g., 0.032 mole) and 2-(aminomethyl)pyridine (3.46 g., 0.032 mole) in 150 ml. of n-pentanol was heated at 130°–135° for 6 hr., cooled and filtered. During reflux, a gas inlet tube can be placed below the solvent surface and dry nitrogen bubbled through the solution to facilitate removal of generated ammonia. The filter-cake washed with 1:2 dioxane-n-hexane yielded 7.8 g. (69%) of the 1,3-dioxoisoindole intermediate (a), m.p. 245°–247°. A sample crystallized from dimethylformamide-ethanol provided analytically pure 6-chloro-2,3-dihydro-1,3-dioxo-2-(2-pyridinylmethyl)-1H-isoindole-5-sulfonamide, m.p. 246°–248°.

Anal. Calcd. for $C_{14}H_{10}ClN_3O_4S$: C, 47.80; H, 2.87; N, 11.94. Found: C, 47.84; H, 3.06; N, 12.08.

A 0.06 mole preparation carried out at temperature (reaction time) 125°–135° (4 hr.), then 100°–110° (16 hr.), and finally 130°–135° (6 hr.) provided an 80% yield of 6-chloro-2,3-dihydro-1,3-dioxo-2-(pyridinylmethyl)-1H-isoindole-5-sulfonamide, m.p. 240°–242°.

(b) Tin-Hydrochloric Acid Reduction of 6-Chloro-2,3-dihydro-1,3-dioxo-2-(2-pyridinylmethyl)-1H-isoindole-5-sulfonamide. A mixture of the above part (a) 1,3-dioxoisoindole (18 g., 0.051 mole), 120 ml. of methanol and 60 ml. of concentrated hydrochloric acid was heated with 30 mesh granulated tin metal added as indicated: 15 g. at 65°–70° for 6 hr., then 8 g. at 60°–65° for 16 hr. and finally 6 g. at 70°–75° for a 7 hr. period. The reaction mixture is cooled, filtered and concentrated to about 60 ml. volume. Addition of about 60 ml. of methanol to the concentrated mixture provided on standing 10 g., of a tin salt complex. This material was further purified by stirring with 1 liter of 50% methanol and 20 ml. of 1N hydrochloric acid while slowly introducing a gaseous stream of hydrogen sulfide ($H_2S$) during a 1 hr. period at 45°–50°. The mixture is stirred at 40°–45° for 16 hr. and then concentrated slightly to remove excess $H_2S$. Activated charcoal was added and the mixture filtered. Concentration of the filtrate to about 50 ml. and dilution with 1 ml. of 6N hydrochloric acid and cooling yielded 2.2 g. (12%) of white solid. Crystallization from aqueous methanol afforded analytically pure 6-chloro-2,3-dihydro-3-oxo-2-(2-pyridinylmethyl)-1H-isoindole-5-sulfonamide as the hydrochloride salt, m.p. 264°–266°.

Anal. Calcd. for $C_{14}H_{12}ClN_3O_3S\cdot HCl$: C, 44.94; H, 3.50; N, 11.23. Found: C, 45.13; H, 3.50; N, 11.42.

NMR (DMSO-$d_6$): 4.70 (2H,s); 5.06 (2H,s); 7.72 (3H,m); 7.95 (1H,s); 8.22 (2H,m); 8.70 (1H,m); 8.90 (1H,bs).

(c) Zinc-acetic acid reduction of 6-chloro-2,3-dihydro-1,3-dioxo-2-(2-pyridinylmethyl)-1H-isoindole-5-sulfonamide. Zinc dust (0.5 mole) is added in one portion to the 1,3-dioxoisoindole (0.1 mole) of part (a) in 800 ml. of acetic acid. The reaction mixture is stirred at room temperature for 1.0 hr. and then heated to reflux for a 6 hr. period during which time additional 9.0 g. portions of zinc are added at the end of 3, 4, and 5 hr., respectively. After stirring overnight, the reaction mixture is filtered and the filtrate concentrated to dryness under reduced pressure with additional water added to the residue and removed in vacuo to remove traces of acetic acid. Residual material is slurried in water, filtered, and the filtrate concentrated to dryness. Residual material is stirred with saturated sodium bicarbonate solution and an immiscible organic solvent such as hot ethyl acetate. The organic fraction is separated, dried over MgSO$_4$ and concentrated to provide the product as the free base. The free base taken up in dimethylformamide and acidified with ethanolic hydrogen chloride affords 6-chloro-2,3-dihydro-3-oxo-2-(2-pyridinylmethyl)-1H-isoindole-5-sulfonamide hydrochloride.

EXAMPLE 2

6-Chloro-2,3-dihydro-3-oxo-2-(3-pyridinylmethyl)-1H-isoindole-5-sulfonamide

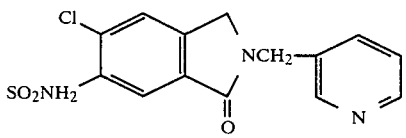

(a) 6-Chloro-2,3-dihydro-1,3-dioxo-2-(3-pyridinylmethyl)-1H-isoindole-5-sulfonamide. Reaction of a mixture of 4-chloro-5-sulfamoylphthalimide and 3-(aminomethyl)pyridine according to the procedure of Example 1(a) afforded a 73% yield of the 1,3-dioxoisoindole intermediate. Crystallization of this material from dimethylformamide-methanol provided analytically pure 6-chloro-2,3-dihydro-1,3-dioxo-2-(3-pyridinylmethyl)-1H-isoindole-5-sulfonamide, m.p. 210°-212°.

Anal. Calcd. for $C_{14}H_{10}ClN_3O_4S$: C, 47.80; H, 2.87; N, 11.94. Found: C, 48.06; H, 2.95; N, 11.90.

(b) Reduction of the above part (a) 1,3-dioxoisoindole with granulated tin and purification with H$_2$S/dilute hydrochloric acid according to the procedure of Example 1(b) with crystallization of the product (13% yield) from aqueous methanol afforded 6-chloro-2,3-dihydro-3-oxo-2-(3-pyridinylmethyl)-1H-isoindole-5-sulfonamide as the hydrochloride salt, m.p. 278°-280° (dec.).

Anal. Calcd. for $C_{14}H_{12}ClN_3O_3S\cdot HCl$: C, 44.94; H, 3.50; N, 11.23. Found: C, 45.02; H, 3.50; N, 11.30.

NMR (DMSO-$d_6$): 4.61 (2H,s); 4.97 (2H,s); 7.81 (2H,bs); 7.92 (1H,s); 7.96 (1H,m); 8.25 (1H,s); 8.43 (1H,m); 8.84 (2H,m); 9.80 (1H,bs).

EXAMPLE 3

6-Chloro-2,3-dihydro-3-oxo-2-[2-(2-pyridinyl)ethyl]-1H-isoindole-5-sulfonamide

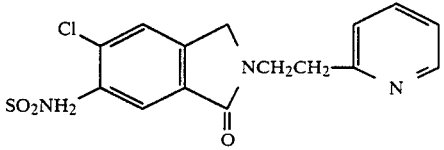

(a) 6-Chloro-2,3-dihydro-1,3-dioxo-2-[2-(2-pyridinyl)ethyl]-1H-isoindole-5-sulfonamide. Reaction of a mixture of 4-chloro-5-sulfamoylphthalimide and 2-(2-aminoethyl)pyridine according to the procedure of Example 1(a) afforded 81% yield of the 1,3-dioxoisoindole intermediate. Crystallization of this material from dimethylformamide-methanol provided analytically pure 6-chloro-2,3-dihydro-1,3-dioxo-2-[2-(2-pyridinyl)ethyl]-1H-isoindole-5-sulfonamide, m.p. 240°-241°.

Anal. Calcd. for $C_{15}H_{12}ClN_3O_4S$: C, 49.25; H, 3.31; N, 11.49. Found: C, 49.50; H, 3.39; H, 11.37.

(b) Reduction of the part (a) 1,3-dioxoisoindole with granulated tin and purification with H$_2$S/dilute hydrochloric acid according to the procedure of Example 1(b) with crystallization of the product (45% yield) from aqueous methanol afforded 6-chloro-2,3-dihydro-3-oxo-2-[2-(2-pyridinyl)ethyl]-1H-isoindole-5-sulfonamide as the hydrochloride salt, m.p. 290°-292° (dec.).

Anal. Calcd. for $C_{15}H_{14}ClN_3O_3S\cdot HCl$: C, 46.40; H, 3.89; N, 10.82. Found: C, 46.32; H, 3.99; N, 10.69.

NMR (DMSO-$d_6$): 3.43 (2H,t, 6.1 Hz); 4.01 (2H,t, 6.1 Hz); 4.72 (2H,s); 7.88 (4H,m); 7.95 (1H,s); 8.06 (1H,s); 8.41 (1H,m); 8.71 (1H,dd, 1.2 Hz, 5.1 Hz).

EXAMPLE 4

6-Chloro-2,3-dihydro-3-oxo-2-[2-(4-pyridinyl)ethyl]-1H-isoindole-5-sulfonamide (a) 6-Chloro-2,3-dihydro-1,3-dioxo-2-[2-(4-pyridinyl)ethyl]-1H-isoindole-5-sulfonamide. Reaction of a mixture of 4-chloro-5-sulfamoylphthalimide and 4-(2-aminoethyl)pyridine according to the procedure of Example 1(a) afforded a 93% yield of the 1,3-dioxoisoindole intermediate. Crystallization of this material from dimethylformamide provided analytically pure 6-chloro-2,3-dihydro-1,3-dioxo-2-[2-(4-pyridinyl)ethyl]-1H-isoindole-5-sulfonamide, m.p. 277°-278° (dec.).

Anal. Calcd. for $C_{15}H_{12}ClN_3O_4S$: C, 49.25; H, 3.31; N, 11.49. Found: C, 49.33; H, 3.44; N, 11.51.

(b) Reduction of the part (a) 1,3-dioxoisoindole with granulated tin and purification with H$_2$S/dilute hydrochloric acid according to the procedure of Example 1(b) with crystallization of the product (24% yield) from water afforded 6-chloro-2,3-dihydro-3-oxo-2-[2-(4-pyridinyl)ethyl]-1H-isoindole-5-sulfonamide as the hydrochloride salt, m.p. 274°-276°.

Anal. Calcd. for $C_{15}H_{14}ClN_3O_3S\cdot HCl$: C, 46.40; H, 3.89; N, 10.82. Found: C, 46.13; H, 3.86; N, 10.91.

NMR (DMSO-$d_6$): 3.28 (2H,t, 6.1 Hz); 3.92 (2H,t, 6.1 Hz); 4.62 (2H,s); 7.75 (2H,bs); 8.00 (4H,m); 8.78 (2H,m).

EXAMPLE 5

6-Chloro-2,3-dihydro-3-oxo-2-[2-(1-piperidinyl)ethyl]-1H-isoindole-5-sulfonamide

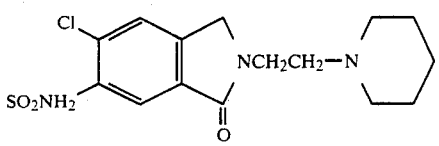

(a) 6-Chloro-2,3-dihydro-2-[2-(1-piperidinyl)ethyl]-1,3-dioxo-1H-isoindole-5-sulfonamide. Reaction of a mixture of 4-chloro-5-sulfamoylphthalimide and 2-(1-piperidinyl)ethylamine according to the procedure of Example 1(a) afforded a 71% yield of the 1,3-dioxoisoindole intermediate, m.p. 200°-202° from ethanol.

(b) Reduction of the part (a) 1,3-dioxoisoindole with granulated tin and purification with H$_2$S/dilute hydrochloric acid according to the procedure of Example 1(b) with crystallization of the product (21% yield) from aqueous methanol provided analytically pure 6-chloro-2,3-dihydro-3-oxo-2-[2-(1-piperidinyl)ethyl]-1H-isoindole-5-sulfonamide as the hydrochloride salt, m.p. 284°-286° (dec.).

Anal. Calcd. for C$_{15}$H$_{20}$ClN$_3$O$_3$S.HCl: C, 45.69; H, 5.37; N, 10.66. Found: 45.74; H, 5.36; N, 10.50.

NMR (DMSO-d$_6$): 1.79 (6H,m); 2.95 (2H,m); 3.45 (4H,m); 3.99 (2H,t, 6.0 Hz); 4.70 (2H,s); 7.82 (2H,bs); 7.99 (1H,s); 8.22 (1H,s).

EXAMPLE 6

6-Chloro-2,3-dihydro-2-[2-(4-morpholinyl)ethyl]-3-oxo-1H-isoindole-5-sulfonamide

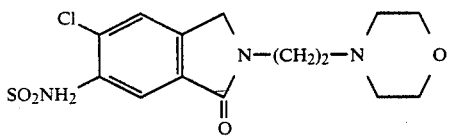

(a) 6-Chloro-2,3-dihydro-2-[2-(4-morpholinyl)ethyl]-1,3-dioxo-1H-isoindole-5-sulfonamide. Reaction of a mixture of 4-chloro-5-sulfamoylphthalimide (2.5 g., 0.0096 mole) and N-(2-aminoethyl)morpholine (1.25 g., 0.096 mole) in 25 ml. of 2-methyl-1-butanol at 145°-150° (oil bath temperature) for 4 hr. according to the procedure of Example 1(a) afforded 3.6 g. (100%) of the 1,3-dioxoisoindole intermediate as a tan solid. A sample crystallized from ethanol provided analytically pure 6-chloro-2,3-dihydro-2-[2-(4-morpholinyl)ethyl]-1,3-dioxo-1H-isoindole-5-sulfonamide, m.p. 218°-219°.

Anal. Calcd. for C$_{14}$H$_{16}$ClN$_3$O$_5$S: C, 44.99; H, 4.31; N, 11.24. Found: C, 45.22; H, 4.41; N, 11.33.

(b) Reduction of the above part (a) 1,3-dioxoisoindole (5.6 g., 0.015 mole) with granulated tin and purification with H$_2$S/dilute hydrochloric acid according to the procedure of Example 1(b) with crystallization of the product (8% yield) from aqueous methanol afforded 6-chloro-2,3-dihydro-2-[2-(4-morpholinyl)ethyl]-3-oxo-1H-isoindole-5-sulfonamide as the hydrochloride hemihydrate, m.p. 294°-296° (dec.).

Anal. Calcd. for C$_{14}$H$_{18}$ClN$_3$O$_4$S.HCl.0.5H$_2$O: C, 41.49; H, 4.97; N, 10.37; H$_2$O, 2.22. Found: C, 41.80; H, 5.01; N, 10.37; H$_2$O, 1.58.

NMR (DMSO-d$_6$): 3.19 (1H,m); 3.48 (6H,m); 3.93 (6H,m); 4.70 (2H,s); 7.81 (2H,bs); 8.00 (1H,s); 8.24 (1H,s); 11.50 (1H,bs).

Repeating the reduction of the Part (a) 1,3-dioxoisoindole (11.5 g., 0.031 mole) with metallic tin and hydrochloric acid and removal of residual ionic tin by treatment with H$_2$S under acidic conditions provided 6-chloro-2,3-dihydro-2-[2-(4-morpholinyl)ethyl]-3-oxo-1H-isoindole-5-sulfonamide as the hydrochloride salt with 0.15 mole equivalent of water, m.p. 298°-300° (dec.).

Anal. Calcd. for C$_{14}$H$_{18}$ClN$_3$O$_4$S.HCl.0.15H$_2$O: C, 42.14; H, 4.88; N, 10.53; H$_2$O, 0.68. Found: C, 42.32; H, 4.94; N, 10.38; H$_2$O, 0.92.

NMR (DMSO-d$_6$): 3.20 (1H,m); 3.47 (6H,m); 3.94 (6H,m); 4.70 (2H,s); 7.81 (2H,bs); 7.97 (1H,s); 8.21 (1H,s).

The degree of hydration for the compounds of the invention is generally dependent upon drying conditions and usually within the range of ¼ to 1.5 mole equivalent of water.

EXAMPLE 7

6-Chloro-2,3-dihydro-2-[3-(4-morpholinyl)propyl]-3-oxo-1H-isoindole-5-sulfonamide

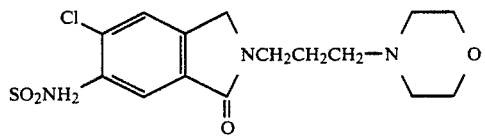

(a) 6-Chloro-2,3-dihydro-2-[3-(4-morpholinyl)propyl]-1,3-dioxo-1H-isoindole-5-sulfonamide. Reaction of a mixture of 4-chloro-5-sulfamoylphthalimide and N-(3-aminopropyl)morpholine according to the procedure of Example 1(a) afforded a 92% yield of the 1,3-dioxoisoindole intermediate. Crystallization of this material from 80% aqueous ethanol provided analytically pure 6-chloro-2,3-dihydro-2-[3-(4-morpholinyl)propyl]-1,3-dioxo-1H-isoindole-5-sulfonamide, m.p. 190°-191°.

Anal. Calcd. for C$_{15}$H$_{18}$ClN$_3$O$_5$S: C, 46.46; H, 4.68; N, 10.84. Found: C, 46.47; H, 4.56; N, 10.92.

(b) Reduction of the above part (a) 1,3-dioxoisoindole with granulated tin and purification with H$_2$S/dilute hydrochloric acid according to the procedure of Example 1(b) with crystallization of the product (28% yield) from aqueous methanol afforded 6-chloro-2,3-dihydro-2-[3-(4-morpholinyl)propyl]-3-oxo-1H-isoindole-5-sulfonamide as the hydrochloride salt, m.p. 212°-214°.

Anal. Calcd. for C$_{15}$H$_{20}$ClN$_3$O$_4$S.HCl: C, 43.91; H, 5.16; N, 10.24. Found: C, 43.93; H, 5.28; N, 10.31.

NMR (DMSO-d$_6$): 2.15 (2H,m); 3.05 (4H,m); 3.35 (2H,m); 3.64 (2H,t, 6.0 Hz); 3.90 (4H,m); 4.63 (2H,s); 7.78 (2H,bs); 7.96 (1H,s); 8.20 (1H,s); 11.60 (1H,bs).

EXAMPLE 8

6-Chloro-2-[2-(diethylamino)ethyl]-2,3-dihydro-3-oxo-1H-isoindole-5-sulfonamide

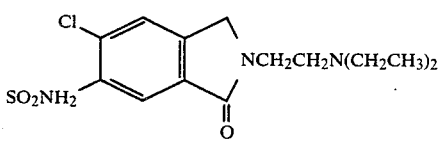

(a) 6-Chloro-2-[2-(diethylamino)ethyl]-2,3-dihydro-1,3-dioxo-1H-isoindole-5-sulfonamide. Reaction of a mixture of 4-chloro-5-sulfamoylphthalimide and 2-(diethylamino)ethylamine according to the procedure of Example 1(a) afforded a 50% yield of the 1,3-dioxoisoindole intermediate. Crystallization of this material from dimethylformamide-ethanol provided analytically pure 6-chloro-2-[2-(diethylamino)ethyl]-2,3-dihydro-1,3-dioxo-1H-isoindole-5-sulfonamide, m.p. 152°–154°.

Anal. Calcd. for $C_{14}H_{18}ClN_3O_4S$: C, 46.74; H, 5.04; N, 11.68. Found: C, 46.75; H, 5.06; N, 11.50.

(b) Reduction of the above part (a) 1,3-dioxoisoindole with granulated tin and purification with $H_2S$/dilute hydrochloric acid according to the procedure of Example 1(b) with crystallization of the product (10% yield) from aqueous methanol afforded 6-chloro-2-[2-diethylamino)ethyl]-2,3-dihydro-3-oxo-1H-isoindole-5-sulfonamide as the hydrochloride salt, m.p. 272°–274° (dec.).

Anal. Calcd. for $C_{14}H_{20}ClN_3O_3S\cdot HCl$: C, 44.00; H, 5.52; N, 10.99. Found: C, 43.68; H, 5.96; N, 10.84.

NMR (DMSO-$d_6$): 1.26 (6H,t, 7.0 Hz); 3.26 (6H,m); 3.97 (2H,t, 6.0 Hz); 4.70 (2H,s); 7.82 (2H,bs); 7.96 (1H,s); 8.21 (1H,s).

EXAMPLE 9

6-Chloro-2-[3-(dimethylamino)propyl]-2,3-dihydro-3-oxo-1H-isoindole-5-sulfonamide

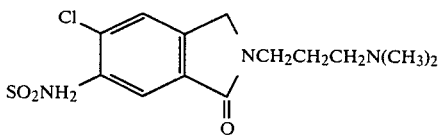

(a) 6-Chloro-2-[3-(dimethylamino)propyl]-2,3-dihydro-1,3-dioxo-1H-isoindole-5-sulfonamide. Reaction of a mixture 4-chloro-5-sulfamoylphthalimide and 3-(dimethylamino)propylamine according to the procedure of Example 1(a) afforded a 95% yield of the 1,3-dioxoisoindole intermediate. Crystallization of this material from dimethylformamide-ethanol provided analytically pure 6-chloro-2-[3-(dimethylamino)propyl]-2,3-dihydro-1,3-dioxo-1H-isoindole-5-sulfonamide, m.p. 192°–194°.

Anal. Calcd. for $C_{13}H_{16}ClN_3O_4S$: C, 45.15; H, 4.66; N, 12.15. Found: C, 45.26; H, 4.76; N, 12.38.

(b) Reduction of the above part (a) 1,3-dioxoisoindole with granulated tin and purification with $H_2S$/dilute hydrochloric acid according to the procedure of Example 1(b) with crystallization of the product (21% yield) from aqueous methanol afforded 6-chloro-2-[3-(dimethylamino)propyl]-2,3-dihydro-3-oxo-1H-isoindole-5-sulfonamide salt, m.p. 287°–288° (dec.).

Anal. Calcd. for $C_{13}H_{18}ClN_3O_3S\cdot HCl$: C, 42.40; H, 5.20; N, 11.41. Found: C, 42.19; H, 5.22; N, 11.48.

NMR (DMSO-$d_6$): 2.08 (2H,m); 2.69 (6H,s); 3.00 (2H,m); 3.61 (2H,t, 6.2 Hz); 4.61 (2H,s); 7.79 (2H,bs); 7.95 (1H,s); 8.20 (1H,s).

EXAMPLE 10

6-(Trifluoromethyl)-2,3-dihydro-3-oxo-2-[2-(4-morpholinyl)ethyl]-3-oxo-1H-isoindole-5-sulfonamide

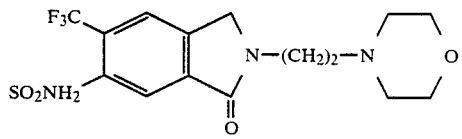

Substituting 4-(trifluoromethyl)-5-sulfamoylphthalimide for 4-chloro-5-sulfamoylphthalimide in the procedure of Example 6(a), provides 6-(trifluoromethyl)-2,3-dihydro-2-[2-(4-morpholinyl)ethyl]-1,3-dioxo-1H-isoindole-5-sulfonamide.

Reduction of the 1,3-dioxoisoindole intermediate according to Example 6(b) affords 6-(trifluoromethyl)-2,3-dihydro-2-[2-(4-morpholinyl)ethyl]-3-oxo-1H-isoindole-5-sulfonamide as the hydrochloride salt.

EXAMPLE 11

6-Chloro-2,3-dihydro-2-[2-[N-methyl-N-(phenylmethyl)amino]ethyl]-3-oxo-1H-isoindole-5-sulfonamide

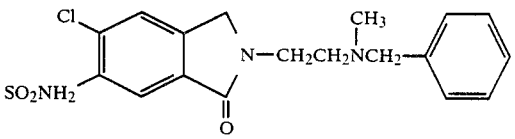

(a) N-[2-[N-Methyl-N-(phenylmethyl)amino]ethyl]phthalimide. A mixture of N-(2-bromoethyl)phthalimide (15.0 g., 0.059 mole), N-methylbenzylamine (7.2 g., 0.059 mole) and potassium carbonate (17.95 g., 0.13 mole) in 140 ml. of acetonitrile was refluxed under a nitrogen atmosphere for a 16 hr. period. Filtration of the hot reaction mixture and concentration of the filtrate under reduced pressure provided 17.2 g. (99.2% yield) of N-[2-[N-methyl-N-(phenylmethyl)amino]ethyl]phthalimide.

(b) 2-[N-Methyl-N-(phenylmethyl)]ethylamine. Hydrazine hydrate (99%, 1.88 g., 0.0585 mole) was slowly added to N-[2-[N-methyl-N-(phenylmethyl)amino]ethyl]phthalimide (17.22 g., 0.0585 mole) and the mixture then stirred for 15 min. and refluxed for a 24 hr. period. The reaction was filtered, made basic with 1N sodium hydroxide to pH 10 and extracted with portions of chloroform. The combined chloroform extracts were first dried and then concentrated to provide 11.8 g. of 2-[N-methyl-N-(phenylmethyl)]ethylamine as a viscous yellow oil.

(c) 6-Chloro-2,3-dihydro-1,3-dioxo-2-[2-[N-methyl-N-(phenylmethyl)]ethyl]-1H-isoindole-5-sulfonamide. Reaction of 4-chloro-5-sulfamoylphthalimide (9.5 g., 0.0365 mole) and 2-[N-methyl-N-(phenylmethyl)]ethylamine (6.0 g., 0.0365 mole) in 200 ml. of amyl alcohol at reflux temperature for a 24 hr. period under nitrogen according to the procedure of Example 1(a) afforded a 57% yield of the 1,3-dioxoisoindole intermediate, m.p. 182°–187° C.

(d) Reduction of the above step (c) 1,3-dioxoisoindole (7.9 g., 0.194 mole) with zinc dust (6.96 g., 0.1065 mole) according to the procedure of Example 1(c) afforded 2.38 g. (32% yield) of hydrated 6-chloro-2,3-dihydro-2-[2-[N-methyl-N-(phenylmethyl)amino]ethyl]-3-oxo-1H-isoindole-5-sulfonamide, m.p. 178°–179° C.

Anal. Calcd. for $C_{18}H_{20}ClN_3O_3S.0.1H_2O$: C, 54.64; H, 5.15; N, 10.62; $H_2O$, 0.45. Found: C, 54.32; H, 4.98; N, 10.28; $H_2O$, 0.24.

NMR (DMSO-$d_6$): 2.20 (3,s); 2.61 (2,t, 6.1 Hz); 3.50 (2,s); 3.68 (2,t, 6.1 Hz); 4.53 (2,s); 7.18 (5,s); 7.72 (2,bs); 7.90 (1,s); 8.20 (1,s).

EXAMPLE 12

6-Chloro-2,3-dihydro-2-[3-[N-methyl-(N-(phenylmethyl)-amino]propyl]-3-oxo-1H-isoindole-5-sulfonamide

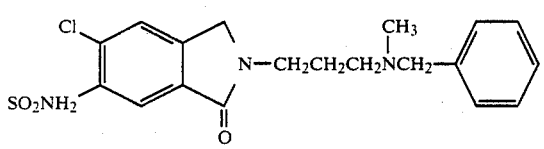

(a) 6-Chloro-2,3-dihydro-1,3-dioxo-2-[3-[N-methyl-N-phenylmethyl]propyl]-1H-isoindole-5-sulfonamide. Reaction of 3-[N-methyl-N-(phenylmethyl)]propylamine (5.0 g., 0.028 mole) obtained in a manner analogous to procedures of Example 11(a)(b) with 4-chloro-5-sulfamoylphthalimide (7.3 g., 0.028 mole) according to the procedure of Example 11(c) afforded 8.8 g. (75% yield) of the 1,3-dioxoisoindole intermediate, m.p. 121°–125° C., purified by chromatography using silica support and 3:2 ethyl acetate-hexane solvent.

(b) Reduction of the above step (a) 1,3-dioxoisoindole (8.7 g., 0.0206 mole) with zinc dust (7.4 g., 0.1135 mole) according to the procedure of Example 1(c) afforded 3.68 g., (40% yield) of product. Crystallization from isopropanol provided 1.38 g. of 6-chloro-2,3-dihydro-2-[3-[N-methyl-N-(phenylmethyl)amino]propyl]-3-oxo-1H-isoindole-5-sulfonamide, m.p. 155°–157° C.

Anal. Calcd. for $C_{19}H_{22}ClN_3O_3S$: C, 55.94; H, 5.44; N, 10.30. Found: C, 55.87; H, 5.43; N, 10.12.

NMR (DMSO-$d_6$): 1.79 (2,m); 2.10 (3,s); 2.35 (2,t, 6.5 Hz); 3.43 (2,s); 3.57 (2,t, 6.6 Hz); 4.51 (2,s); 7.24 (5,s); 7.73 (2,bs); 7.88 (1,s); 8.19 (1,s).

EXAMPLE 13

Compounds of Formula III

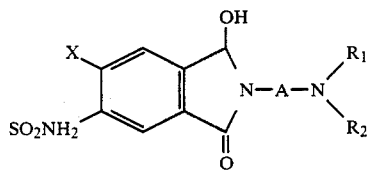

General Procedure. A mixture of 0.05 mole of a Formula II or 1,3-dioxoisoindole of Formula II and 0.28 mole of zinc dust in 500 ml. of glacial acetic acid is stirred at room temperature for 30–60 min. The mixture is filtered, the filtrate concentrated in vacuo and residual material diluted with 1:1 ethyl acetate-aqueous sodium bicarbonate. The layers are separated and the aqueous phase extracted with ethyl acetate. Combined extracts are dried and the 1-hydroxy-3-oxoisoindole product isolated by concentration.

The compounds tabulated below can be prepared according to this procedure from the indicated 1,3-dioxoisoindole starting material.

TABLE 1

| Example No. | 1,3-Dioxo isoindole Example No. | X | A | $-N\begin{smallmatrix}R_1\\R_2\end{smallmatrix}$ |
|---|---|---|---|---|
| 13-1 | 1(a) | Cl | $-CH_2-$ | 2-pyridyl |
| 13-2 | 2(a) | Cl | $-CH_2-$ | 3-pyridyl |
| 13-3 | 3(a) | Cl | $-CH_2CH_2-$ | 3-pyridyl |
| 13-4 | 4(a) | Cl | $-CH_2CH_2-$ | 4-pyridyl |
| 13-5 | 5(a) | Cl | $-CH_2CH_2-$ | piperidino |
| 13-6 | 6(a) | Cl | $-CH_2CH_2-$ | morpholino |
| 13-7 | 7(a) | Cl | $-(CH_2)_3-$ | morpholino |
| 13-8 | 8(a) | Cl | $-CH_2CH_2-$ | $-N(C_2H_5)_2$ |
| 13-9 | 9(a) | Cl | $-(CH_2)_3-$ | $-N(CH_3)_2$ |
| 13-10 | 10 | $CF_3$ | $-CH_2CH_2-$ | morpholino |
| 13-11 | 11(c) | Cl | $-CH_2CH_2-$ | $-N(CH_3)CH_2C_6H_5$ |
| 13-12 | 12(a) | Cl | $-(CH_2)_3-$ | $-N(CH_3)CH_2C_6H_5$ |

What is claimed is:
1. A compound of Formula I

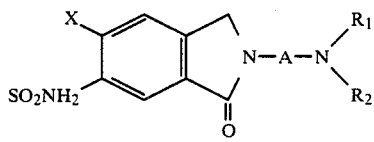

wherein
- X is halogen or trifluoromethyl;
- A is alkylene of 2 to 4 carbon atoms;
- R$_1$ is lower alkyl;
- R$_2$ is lower alkyl or phenylalkyl of 7 to 10 carbon atoms;
- R$_1$ and R$_2$ taken together with nitrogen is piperidino, morpholino or pyridinyl;

or a pharmaceutically acceptable salt thereof.

2. The compound of claim 1 which is 6-chloro-2,3-dihydro-3-oxo-2-(2-pyridinylmethyl)-1H-isoindole-5-sulfonamide.

3. The compound of claim 1 which is 6-chloro-2,3-dihydro-3-oxo-2-(3-pyridinylmethyl)-1H-isoindole-5-sulfonamide.

4. The compound of claim 1 which is 6-chloro-2,3-dihydro-3-oxo-2-[2-(2-pyridinyl)ethyl]-1H-isoindole-5-sulfonamide.

5. The compound of claim 1 which is 6-chloro-2,3-dihydro-3-oxo-2-[2-(4-pyridinyl)ethyl]-1H-isoindole-5-sulfonamide.

6. The compound of claim 1 which is 6-chloro-2,3-dihydro-3-oxo-2-[2-(1-piperidinyl)ethyl]-1H-isoindole-5-sulfonamide.

7. The compound of claim 1 which is 6-chloro-2,3-dihydro-2-[2-(4-morpholinyl)ethyl]-3-oxo-1H-isoindole-5-sulfonamide.

8. The compound of claim 1 which is 6-chloro-2,3-dihydro-2-[3-(4-morpholinyl)propyl]-3-oxo-1H-isoindole-5-sulfonamide.

9. The compound of claim 1 which is 6-chloro-2-[2-(diethylamino)ethyl]-2,3-dihydro-3-oxo-1H-isoindole-5-sulfonamide.

10. The compound of claim 1 which is 6-chloro-2-[3-(dimethylamino)propyl]-2,3-dihydro-3-oxo-1H-isoindole-5-sulfonamide.

11. The compound of claim 1 which is 6-chloro-2,3-dihydro-2-[2-[N-methyl-N-(phenylmethyl)amino]ethyl]-3-oxo-1H-isoindole-5-sulfonamide.

12. The compound of claim 1 which is 6-chloro-2,3-dihydro-2-[3-[N-methyl-N-(phenylmethyl)amino]propyl]-3-oxo-1H-isoindole-5-sulfonamide.

13. The process comprising systemically administering to a mammal in need of diuresis a diuretic effective amount of a compound of claim 1 or a pharmaceutically acceptable salt thereof.

14. The pharmaceutical composition comprising a diuretic amount of a compound of claim 1 or a pharmaceutically acceptable acid addition salt thereof and a pharmaceutical carrier.

* * * * *